United States Patent [19]

Senyei et al.

[11] 4,230,685

[45] Oct. 28, 1980

[54] METHOD OF MAGNETIC SEPARATION OF CELLS AND THE LIKE, AND MICROSPHERES FOR USE THEREIN

[75] Inventors: Andrew E. Senyei; Kenneth J. Widder, both of Chicago, Ill.

[73] Assignee: Northwestern University, Evanston, Ill.

[21] Appl. No.: 15,895

[22] Filed: Feb. 28, 1979

[51] Int. Cl.$^2$ ...................... G01N 31/00; G01N 21/46
[52] U.S. Cl. ........................................ 424/12; 210/222
[58] Field of Search ...................... 424/12, 88; 195/1.8

[56] References Cited

U.S. PATENT DOCUMENTS

| 3,970,518 | 7/1976 | Giaever | 195/1.5 |
| 4,018,886 | 4/1977 | Giaever | 424/12 |

OTHER PUBLICATIONS

Kessler–Dissertation Abst. Int(B), 1976, vol. 37, No. 3, pp. 1172–1173.

*Primary Examiner*—Frederick E. Waddell
*Attorney, Agent, or Firm*—Tilton, Fallon, Lungmus & Chestnut

[57] ABSTRACT

Magneticaly-responsive microspheres having Protein A associated with the outer surfaces thereof are reacted with antibodies selective to the cells, bacteria, or viruses to be separated from a mixed population to attach the antibodies in oriented relation with their Fab arms extending outwardly, and the microspheres are then used in a magnetic separation procedure. The preferred microspheres are prepared from a mixture of albumin, Protein A, and magnetic particles, the microspheres being prepared so that the Protein A is present in the exterior surfaces for antibody binding.

10 Claims, No Drawings

METHOD OF MAGNETIC SEPARATION OF CELLS AND THE LIKE, AND MICROSPHERES FOR USE THEREIN

BACKGROUND AND PRIOR ART

This invention relates to the fractionation of heterogeneous populations of cells or the like to isolate a relatively homogeneous sub-population of a specific cell type. More specifically, the improvement of this invention relates to magnetic sorting of cells, bacteria, or viruses.

A general procedure for magnetic sorting of cells, bacteria, and viruses is disclosed in U.S. Pat. No. 3,970,518, issued July 20, 1976. In that procedure, uncoated particles of a magnetic material, such as iron oxide, are contacted with a high concentration liquid dispersion of the selective antibody, and after sufficient antibody has adhered to the magnetic particles, the coated particles are contacted with the mixed population to be fractionated, the select cell or the like binding to the magnetic particles, and the bound cells are then separated magnetically from the remainder of the population. As a further step, the select cells may be separated from the magnetic material, by the use of a cleaving agent solution and magnetic removal of the magnetic particles.

While there are literature reports describing the use of magnetic microspheres in cell sorting, there is no literature verification that uncoated magnetic particles can be made to effectively bind with antibodies. In the published procedures, the particles of magnetic material are contained in microspheres formed from polymers, which can be chemically coupled to antibodies. See, for example: Molday et al, *Nature*, 268, 437 (1977); Kronick et al, *Science*, 200, 1074 (1978); and Antoine et al, *Immunochemistry*, 15, 443 (1978). These references describe magnetically-responsive microspheres formed from acrylate polymers, such as hydroxyethyl methacrylate, or polyacrylamide-agarose microspheres. Such microspheres can be chemically coupled to antibodies with glutaraldehyde or other di-aldehyde. As described by the cited Molday (1977) and Kornick references, one procedure involves the chemical attachment of diaminoheptane spacer groups to the microspheres, which are then chemically linked to the antibodies by glutaraldehyde reaction. Although effective bonding of the antibodies can be obtained, such procedures are difficult since aggregation of microspheres can readily occur and the preparative procedure is time consuming. For example, the reaction to attach spacer groups may require from five to twelve hours of chemical reaction time, and subsequent dialysis to remove the excess reagent. The coupling of the antibodies may then require another twelve to twenty-four hours followed by dialysis to remove excess coupling agent. Further, such antibody reagents may not be used efficiently, since an excess of the antibodies will usually need to be present during the chemical coupling.

Another disadvantage of magnetic particle or microsphere separation methods as described in the art is that the antibodies are attached to the microspheres in a random manner. Antigen-binding occurs through the Fab regions of the antibodies which are in the outer portions of the arms. With random attachment of the antibodies, one or both of the Fab arms may be unavailable for antigen-binding. thus, an excess of antibody must be used to assure that the coated microspheres effectively bind to the antigens associated with the cells or other bodies being sorted.

SUMMARY OF THE INVENTION

The present invention utilizes staphylococcal Protein A to overcome the limitations of prior art magnetic sorting procedures, as described above. It is known that staphylococcal Protein A selectively binds to antibodies through the Fc region of the antibodies, which is located in the tail portions of the antibodies remote from the Fab arms. See Forsgren et al, *J. Immunol.*, 99, 19 (1977). Heretofore, however, this property of Protein A has not been utilized to form magnetic microspheres. Protein A has been coupled to Sepharose beads (cross-linked agarose gels) to provide a column material with immunoglobulin-binding properties. The column may be used for affinity chromatography, for example, of the IgG fraction of serum. Such chromatographic column materials are commercially available.

Protein A has also been used in procedures for cell separation by density gradient centrifugation. See, for example, Ghetie et al, *Scand. J. Immunol.*, 4, 471 (1975). In a typical procedure, sheep erythrocytes are coated with Protein A by $CrCl_3$ coupling, and the coated erythrocytes are then contacted with mouse lymphocytes which have been previously reacted with antibodies to prepare the cell surfaces for binding to Protein A, thereby resulting in rosetting of the lymphocytes around the erythrocytes. The resulting rosetted cells are recovered by density gradient centrifugation.

In accordance with the present invention, as distinguished from prior art procedures, magnetically-responsive microspheres are prepared having Protein A associated with the surfaces thereof, and the resulting microspheres are first reacted with the select antibodies before the microspheres are used for cell separation. With the microspheres used in the method of this invention the antibodies are thereby arranged in oriented attachment on their outer surfaces with the Fab arms of the antibodies extending outwardly. The effectiveness of the microspheres for antigen binding and use in magnetic sorting procedures is thereby maximized. This greatly increases the efficiency with which the select antibodies may be used. Further, it eliminates the need for chemical coupling of the antibodies.

In a preferred embodiment, the mirospheres are prepared by mixing Protein A with a polymer matrix material which does not mask the antibody-binding sites of the Protein A. The resulting microspheres having the Protein A in the outer surfaces thereof do not require chemical coupling of the Protein A to preformed microspheres. Albumin appears to be a particularly suitable matrix material for preparing such microspheres. When the microspheres are formed from an aqueous admixture of albumin, Protein A, and magnetic particles, the Protein A is effectively available in the outer surfaces of the microspheres, in effect, forming surface layers on the microspheres with the Protein A in high concentration. The explanation for this result is not fully understood, but appears to relate to the wetting agent or surface tension properties of Protein A when dispersed in an aqueous solution in admixture with albumin.

DETAILED DESCRIPTION

It its broad method aspect, the present invention relates to a method for the separation of a select population of cells, bacteria, or viruses from a mixed population thereof, in which the microspheres containing magnetic particles are coated with a layer of antibodies which selectively bind to the select population. The coated microspheres are contacted with the mixed population, and the bound select population is magnetically separated from the rest of the mixed population. The method improvement is characterized by modifying the surfaces of the microspheres prior to coating them with antibodies to provide staphylococcal Protein A distributed thereover in adherent relation to the microspheres. The microspheres are then contacted with antibodies which bind the Protein A and which also bind selectively to the select population. By this means the antibodies are arranged in oriented attachment on the surfaces of the microspheres with their Fab arms extending outwardly. Thereafter, the rest of the steps of the magnetic separation are carried out, as is known in the art. Preferably, the microspheres are formed of a polymer matrix material in admixture with the magnetic particles and Protein A, such as an albumin matrix material in an amount of 100 parts per 5 to 40 parts of Protein A. Alternatively, however, the Protein A may be chemically-bonded to the exterior surfaces of the microspheres to provide a Protein A coating thereon.

Where chemical coupling procedures are used, the microspheres may be formed from any matrix material which can be chemically coupled to Protein A, including albumin or other amino acid polymer, and synthetic polymers, such as acrylate polymers. For example, the microspheres may be formed from methyl methacrylate, hydroxyethyl methacrylate, methacrylic acid, ethylene glycol dimethacrylate, agarose polymers, polyacrylamide polymers, or mixtures of such polymers. Protein A may be directly coupled to solid support surfaces containing magnetically responsive materials by several procedures. See, for example, Molday et al, *J. Cell Biology*, 64, 75 (1975). Microspheres can be derivatized with either aminocaproic acid or diaminoheptane which provide extended functional groups for coupling proteins to insolubilized matrixes. Alternatively, with solid surfaces already containing functionally available groups (i.e. amino groups on albumin microspheres) a direct glutaraldehyde coupling of Protein A may be accomplished.

An alternate preferred procedure is to incorporate the Protein A in the microspheres by admixing it with the matrix material prior to the formation of the microspheres, and carrying out the preparation so that the Protein A is available in the outer surfaces of the microspheres. Suitable procedures for preparing such microspheres will therefore be described, but it should be understood that the present invention in its broad method aspect is not limited to the use of such preferred microspheres.

For use in the present invention, the Protein A can be prepared from *Staphylococcus aureus* by procedures described in the literature. See, for example, Forsgern et al, *J. Immun.*, 97, 822 (1966); and Kronvall et al, *Immunochemistry*, 7, 124 (1970). Staphylococcal Protein A is also available from commercial sources, such as Pharmacia Fine Chemicals, Piscataway, New Jersey.

The preferred matrix material for forming the microspheres by admixture with Protein A is an amino acid polymer, such as albumin. Animal or human albumin may be used, for example, human serum albumin. Other water-soluble proteins can be used such as hemoglobin, or synthetic amino acid polymers including poly-L-lysine and poly-L-glutamic acid.

When the Protein A is premixed with the matrix polymer, and the microspheres formed therefrom, sufficient Protein A should be included so that the outer surfaces of the microspheres will bind antibodies through the selective action of the Protein A. In general, the microspheres may contain from 2 to 40 parts by weight of Protein A per 100 parts of the matrix polymer such as albumin. Preferred proportions are from about 10 to 35 parts of the Protein A per 100 parts of the matrix polymer.

A sufficient amount of finely-divided particles of a magnetic material should also be included so that the microspheres are magnetically-responsive. For example, the magnetic particles may be ferri- or ferro-magnetic compounds, such as magnetic iron oxides. Other useable magnetic materials in particulate form are disclosed in U.S. Pat. No. 3,970,518. A preferred magnetic material is magnetite ($Fe_3O_4$). Depending on the size of the microspheres, the magnetic particles may range in size from 100 to 20,000 Angstroms. The microspheres may contain from 10 to 150 parts by weight of the magnetic material per 100 parts of the matrix polymer. The microspheres may range in size from 0.2 to 100 microns in diameter. Preferably, however, the microspheres have an average size in the range from about 0.5 to 2.0 microns. With microspheres in this size range, it is preferred that the magnetic particles have diameters of not over 300 Anstroms, such as an average size of about 100 Angstroms.

The procedure previously published for preparing albumin microspheres can be used. Widder et al, *J. Pharm. Sci.*, 68, 79 (1979). The preferred procedure is the one described for the heat-stabilized microspheres. In general, an aqueous mixture is prepared for use in forming the microcapsules, the mixture containing the albumin or other hydrocolloid matrix polymer, Protein A, and the magnetic particles. The solid materials are dispersed in water and thoroughly mixed therewith, for example, using 20 to 40 parts of total solids per 100 parts of water. Sufficient water should be present to form an aqueous gel with the matrix hydrocolloid. In general, the amount of water may range from 10 to 60 part per 100 parts of total solids. The aqueous mix is then emulsified with an oil, such as a vegetable oil, the emulsification being carried out with vigorous agitation, for example, using sonication, to obtain a droplet dispersion of the aqueous mix in the vegetable oil having the requisite droplet size to form the microspheres. Preferably, the emulsification is carried out at low temperatures, such as temperatures in the range of 20° to 30° C. After the emulsion has been formed, the emulsion is added to a larger body of oil, which is preferably the same oil used to form the emulsion. In practice, cottonseed oil gives good results. To promote the separation of the water droplets, the emulsion can be added in small increments to the oil bath, such as by dropwise addition. Preferably, also, the addition is accompanied by rapid stirring of the oil into which the emulsion is being introduced.

For purpose of the present invention, the droplets may be heat-hardened to stabilize them and thereby provide the microspheres. This can be conveniently accomplished by using a heated oil bath, that is, by dispersing the emulsion into hot oil, such as oil at a temperature in the range of 70° to 160° C. The effect of heat stabilization on albumin microspheres is described in U.S. Pat. No. 3,937,668, issued Feb. 10, 1976.

After the heat-hardening, the prepared microspheres are separated from the oil. This may be accomplished by centrifugation or filtration, and the microspheres washed with a suitable organic solvent, such as diethyl ether, to remove the oil from the exterior surfaces of the microspheres. The microspheres are then ready for reaction with a specific antibody, such as an antibody prepared in rabbits. Such rabbit immunoglobulins which bind to Protein A include all subclasses of IgG. However antibodies prepared from other sources can be used, providing they also bind to Protein A. Usually, the antibodies will be applied to the microspheres in aqueous suspension. The concentration of the antibodies may be low, since the Protein A will remove the antibodies from the treating solution even at low concentrations. As previously described, the binding is through the Fc region of the antibodies, thereby providing for an oriented attachment of the antibodies with the antigen-binding Fab arms extending outwardly from the outer surfaces of the microspheres. The microspheres are then ready for use in magnetic cell separation, as previously described in the literature.

The magnetic sorting method of this invention and the preferred microspheres for use therein are further described and illustrated in the following specific examples. For conciseness of description, the examples use certain abbreviations, which have the following meanings:

SpA: Staphylococcal Protein A
FITC: flurocein isothiocyanate
CRBC: chicken red blood cell
SRBC: sheep red blood cell
RBC: red blood cell
FCS: fetal calf serum
HBSS: Hank's balanced saline solution
EDC: carbodiimide: 1-cyclohexyl-3-(2-morpholinyl)-(4)-ethyl-carbodiimide methotoluene sulphonate)

EXAMPLE I

Magnetic albumin microspheres containing staphylococcal Protein A (SpA) as part of the matrix were prepared by an emulsion polymerization method. A 0.5 ml aqueous suspension containing a total of 190 mg dry material was made consisting of 66% human serum albumin, 19% $Fe_3O_4$ (particles 15–20 nm) and 15% SpA. To this, 60 ml of cottonseed oil was added and the emulsion was homogenized by sonication for one minute. The homogenate was added dropwise to 200 ml of constantly stirred cottonseed oil at 120° to 125° C. for 10 minutes. The suspension was washed four times in diethyl ether by centrifugation for 15 minutes at 2000 xg and stored at 4° C. until subsequent use. A sample of microspheres were coupled with FITC-conjugated rabbit IgG by incubation at 37° C. for 20 minutes, and examined for surface fluorescence with a fluorescent microscope. The intensity and apparent uniform distribution of fluorescence indicated that SpA was oriented on the microsphere surface in a manner that allowed IgG molecules to interact with the Fc binding sites on the SpA.

EXAMPLE II

Microspheres prepared as described in Example I were used to separate CRBC from suspensions containing both CRBC and SRBC. Aliquots of CRBC and SRBC were labeled with $^{51}Cr$ in order to assess extent of separation as well as cell integrity. Labeling of CRBC was accomplished by incubating $1\times10^8$ CRBC suspended in 0.2 in Hanks balanced salt solution (HBSS) containing 2.5% heat inactivated fetal calf serum (FCS) with 100 $\mu$Ci $Na_2{}^{51}CrO_4$ (1 mCi/ml) for 90 minutes at 37° C. SRBC were labeled by similar treatment with the exception of overnight incubation at 37° C. Antibody was coupled to the microspheres by incubating 0.5 mg of the microspheres suspended in 0.2 ml of 0.9% NaCl solution containing 0.1% Tween 80 (saline-Tween 80) with either 0.5 mg rabbit anti-chicken RBC (IgG fraction) or 0.5 mg normal rabbit IgG for 45 minutes at 37° C. Unbound IgG was removed by centrifugation with excess saline-Tween 80 at 1500 × g for two minutes at 4° C. Microspheres were then resuspended in 0.2 ml saline-Tween 80 by briefly sonicating in an ultrasonic waterbath. To this suspension, a mixture of $1\times10^6$ CRBC and $1\times10^6$ SRBC in 0.2 ml of HBSS was added. The cells were then incubated with the IgG-coated microspheres for 30 minutes at 37° C. with mild agitation. Cells bearing adherent magnetic microspheres were removed from suspension by applying a 4000 gauss (gradient—1500 gauss/cm) bar magnet to the side of each test tube for one minute. Both supernatant and pellet fractions were counted in a Beckman Model 8000 gamma counter for $^{51}Cr$. Control labeled cells, incubated in saline-Tween 80, were counted for $^{51}Cr$ to assess spontaneous release.

Based on $^{51}Cr$ counts, it was found that when $1\times10^6$ $_{51}Cr$ CRBC in combination with $1\times10^6$ SRBC were incubated with 0.5 mg microspheres bearing anti-CRBC antibodies, 97.8% of the labeled cells were magnetically removed from suspension. Hemocytometer counts of erythrocytes in the supernatant revealed only 0.26% residual CRBC among the remaining SRBC. Using this method of cell separation, a population of SRBC which was 97–99% homogeneous was generated with 90.5% recovery of the starting SRBC mass. The non-specific adherence of $^{51}Cr$ CRBC was tested while using microspheres bearing anti-SRBC and normal rabbit IgG respectively, and found to be <10%.

EXAMPLE III

Microspheres prepared as described in Example I were used to fractionate Lewis rat splenocytes. Based on the presence or absence of surface immunoglobulins, it is possible to distinguish between thymus-derived T lymphocytes and bonemarrow derived B lymphocytes. Normal non-IgG bearing splenocytes, considered to be predominantly T lymphocytes, were purified by incubating splenocytes with microspheres containing rabbit anti-rat IgG.

A cellular suspension of spleen cells was obtained by teasing rat spleen on a metal screen in HBSS with 10% heat inactivated FCS. The cells were washed three times and overlayered on Ficoll-Hypaque (specific gravity 1.072). The gradient was then centrifuged at 1200 × g for 25 minutes at 25° C., to eliminate dead cells and red blood cells. The resultant interface band was removed and assessed for viability by trypan blue dye exclusion. The number of IgG bearing cells was determined by incubating the cells at 37° C. with FITC conjugated rabbit anti-rat IgG and counting the number of fluoroscent labeled cells. Rabbit anti-rat IgG, normal rabbit IgG, and rabbit anti-chicken RBC were coupled to 0.5 mg the SpA microspheres (0.5 mg IgG/0.5 mg microspheres). Spenocytes ($2\times10^6$) suspended in HBSS with 2.5% heat inactivated FCS were added to the 0.5 mg microspheres. In order to minimize the capping phenomenon and maintain viability, reaction mixtures were incubated for 2.5 hours at 4° C. Cells with adherent microspheres were separated magnetically as described in Example II, and resultant supernatants were analyzed for total cell count, viability, and fluorescence. The results are summarized in Table A.

Viability of unfractionated cells after centrifugation in Ficoll-Hypaque was 96%. Supernatant cell viability after magnetic separation was 93%, demonstrating a minimal loss of viability. Between 47 to 51% of unfractionated splenocytes were IgG-bearing cells as determined by fluorescence microscopy. However, after magnetic separation of splenocytes in the experimental group, only 0.5% of the supernatant cells had detectable IgG on their surface, showing a highly enriched population of non-IgG-bearing lymphocytes.

Antibody specificity was verified by demonstrating negligible depletion of IgG-bearing cells following incubation of splenocytes with microspheres containing either normal rabbit IgG or anti-CRBC. Rat thymocytes, normally containing 4 to 6% IgG bearing lymphocytes, were totally depleted of these cells after incubation with microspheres coupled with anti-rat IgG.

The sensitivity of the system was tested by serial dilutions of microspheres bearing rabbit anti-chicken RBC with the addition of $1 \times 10^6$ $^{51}$Cr CRBC at each dilution. Incubation of microspheres and cells was carried out for 30 minutes at 37° C. Cells with adherent microspheres were magnetically removed and both pellet and supernatant fractions counted for $^{51}$Cr. Percent CRBC bound to the microspheres was linearly related to the amount of microspheres present until microsphere saturation occured. No less than 99% binding of $1 \times 10^6$ CRBC was observed wen $\geq 104$ μg of microspheres were used.

TABLE A

Separation of Rat T and B Lymphoid Cells Using Antibodies Coupled to SpA-Bearing Magnetic Microspheres.
(Results represent two different experiments done in triplicate and expressed as mean ± S.D.)

| Antibody coupled to microspheres | Type of cell suspension[1] | % of total cells bound to microspheres | % of IgG bearing cells remaining in supernatant after magnetic separation[2] |
|---|---|---|---|
| Rabbit anti-rat IgG | Splenocytes | 50 ± 0.5 | 0.5 |
| Rabbit anti-rat IgG | Thymocytes | 15 ± 1 | 0 |
| Normal rabbit IgG | Splenocytes | 10 ± 0.3 | 47.4 ± 1.2[3] |
| Rabbit anti-CRBC | Splenocytes | 6.5 ± 2 | 44 ± 1.8[3] |

Footnotes to Table A
[1] $2 \times 10^9$ cells/0.2 ml HBSS + 2.5% FCS, incubated with 0.5 mg microspheres bearing antibody as indicated. The reaction mixture was incubated for 2.5 hours at 4° C.
[2] The percent of IgG-bearing cells not removed by magnetic microspheres was determined by incubating supernatant cells with 0.1 ml FITC conjugated rabbit anti-rat IgG for 20 minutes at 37° C. The amount of contaminant IgG-bearing cells was determined by fluorescence microscopy. In addition, 95.3% of the expected non-IgG-bearing splenocytes was found in the supernatant as determined by triplicate counts in a hemocytometer of non-fluorescent cells.
[3] Between 44 to 51% starting splenocytes are IgG-bearing cells as determined by fluorescence microscopy, and 4 to 6% of rat thymocytes are IgG-bearing cells as determined by the same method.

EXAMPLE IV

Magnetic albumin microspheres were prepared as described in Example I, except that Protein A was omitted. The amount of albumin was correspondingly increased so that the dry material used to form the microspheres was 81% albumin and 19% $Fe_3O_4$. Protein A can be applied to the microspheres thus formed as described in Example V.

EXAMPLE V 5 mg/ml Protein A in HBSS is prepared as a starting solution. For the one step aqueous carbodiimide coupling 10 mg of EDC is added to 20 mg of either an acrylate polymer microsphere matrix prederivatized with ε aminocaproic acid, or 20 mg of albumin microspheres suspended in 10 mls of the starting Protein A solution and allowed to react for 4 hrs at 4° C. with vigorous stirring. The coupling reaction is then terminated by addition of 0.4 ml of 0.2 M glycine solution pH 7.9. Unbound Protein A and unreacted EDC is removed by washing 4X in HBSS. The Protein A coated microspheres are then coupled to appropriate antisera by incubation of 2 mg of microspheres with 1 ml of antiserum at 37° C. for 10 mins with slight agitation. The alternative coupling agent is glutaraldehyde 1.25% solution which is added to 10 mls of HBSS solution (pH 7.4) containing 50 mg Protein A and 20 mg of either albumin microspheres or 20 mg of diaminoheptane derivatized acrylate microspheres, allowed to react for 2 hrs at 37° C. with slight agitation. Unreacted Protein A and excess glutaraldehyde is removed by centrifugation washing 4 × with HBSS. Antibody is attached to microspheres as described above in prior examples.

We claim:
1. A method for the separation of a select population of cells, bacteria, or viruses from a mixed population thereof, in which microspheres containing magnetic particles are coated with a layer of antibodies which selectively bind to the select population, the coated microspheres are contacted with said mixed population so that said microspheres are bound to the select population, and said bound select population is magentically separated from the rest of said mixed population, wherein the improvement comprises: prior to coating said microspheres with antibodies modifying the surfaces of said microspheres to provide staphylococcal Protein A distributed thereover in adherent relation to said microspheres, then contacting said microspheres with antibodies which bind to Protein A and which also bind selectively to said select population, whereby said antibodies are arranged in oriented attachment on the surfaces of said microspheres with their Fab arms extending outwardly, and thereafter carrying out the rest of the steps of said method.

2. The method of claim 1 in which said microspheres are formed of a polymer matrix material in admixture with said magnetic particles and said Protein A.

3. The method of claim 2 in which said matrix material is albumin and said microspheres contain from 2 to 40 parts by weight of Protein A per 100 parts of albumin.

4. The method of claim 1 in which said Protein A is chemically-bonded to the exterior surfaces of said microspheres.

5. Microspheres for magnetically sorting of cells, bacteria, or viruses, comprising microspheres formed from an amino acid polymer matrix material in admixture with staphylococcal Protein A, and being of a size from 0.2 to 100 microns diameter, said microspheres containing from 2 to 40 parts by weight of said Protein A per 100 parts of said amino acid polymer and said Protein A being present in the exterior surfaces of said microspheres for antibody binding, said microspheres also containing magnetic particles of a size from 100 to 20,000 Angstroms and in an amount sufficient to make said microspheres magnetically-responsive.

6. The microspheres of claim 5 in which said amino acid polymer is albumin.

7. The microspheres of claim 5 or claim 6 in which said Protein A is present in an amount of from 10 to 30 parts by weight per 100 parts of said amino acid polymer.

8. Microspheres for magnetically sorting of cells, bacteria, or viruses, comprising microspheres formed from an aqueous mixture of albumin, staphylococcal Protein A, and magnetic particles, said microspheres having an average diameter of from 0.5 to 2.0 microns, and containing from 2 to 40 parts of said Protein A per 100 parts of said albumin and said Protein A being present in the exterior surfaces of said microspheres for antibody binding, said magnetic particles being of a size not over 300 Angstroms and being present in an amount sufficient to make said microspheres magnetically-responsive.

9. The microspheres of claim 8 in which said magnetic particles are $Fe_3O_4$ and are present in an amount of from 10 to 150 parts by weight per 100 parts of said albumin.

10. The microspheres of claim 8 or claim 9 in which said Protein A is present in an amount of from 10 to 35 parts by weight per 100 parts of said albumin.

* * * * *